United States Patent
Faunce

[11] 3,936,939
[45] Feb. 10, 1976

[54] VENEER SUPPORTED ORTHODONTIC APPLIANCE

[76] Inventor: Frank R. Faunce, 1307 Wilcrest Drive - Apt. 237, Houston, Tex. 77042

[22] Filed: June 28, 1974

[21] Appl. No.: 493,973

[52] U.S. Cl. .............................................. 32/14 A
[51] Int. Cl.² ........................................ A61C 7/00
[58] Field of Search .................................. 32/14 A

[56] References Cited
UNITED STATES PATENTS

| | | | |
|---|---|---|---|
| 3,345,745 | 10/1967 | Muller | 32/14 A |
| 3,464,114 | 9/1969 | Brader | 32/14 A |
| 3,638,312 | 2/1972 | Szware | 32/14 A |
| 3,765,091 | 10/1973 | Northcutt | 32/14 A |

*Primary Examiner*—Robert Peshock

[57] ABSTRACT

An orthodontic appliance according to the present invention may incorporate a thin veneer body of non-metallic material that may be flexible so as to conform readily to the external configuration of a patient's tooth and which veneer body may be bonded directly to the enamel of the tooth in any desirable manner. An orthodontic appliance which may be composed of metal may be permanently embedded within the thin veneer body and may protrude from the veneer body to enable other orthodontic devices to be attached thereto. Marginal leakage between the veneer body and the enamel surface of the tooth is effectively prevented by the use of a dental sealer material.

13 Claims, 10 Drawing Figures

VENEER SUPPORTED ORTHODONTIC APPLIANCE

FIELD OF THE INVENTION

This invention relates generally to orthodontics and to orthodontic appliances for attachment to the teeth of a patient and more particularly the invention is directed to an orthodontic appliance assembly that may be bonded to the enamel of a patient's tooth structure and may be connected to other orthodontic devices for application of forces to the teeth of the patient.

BACKGROUND OF THE INVENTION

Orthodontics is that branch of dentistry concerned with the study of the growth of craniofacial complex, the development of occlusion, and the treatment of dentofacial abnormalities. Orthodontic therapy is directed to abnormal occlusion of the teeth, growth of the complex of craniofacial bones and the function of the orofacial neuromusculature, which alone or in combination may cause any of a number of abnormalities such as impaired mastication, undesirable facial aesthetics, dysfunction of the temporomandibular articulation, susceptibility to periodontal disease, susceptibility to dental caries, and impaired speech due to the malpositions of the teeth etc. By means of suitable appliances, the individual teeth of the patient can be positioned more favorably to provide better aesthetics, occlusal function, oral health and speech.

Movement of teeth within the bone structure defined by the craniofacial skeletal structure of the patient may be accomplished in many different ways. One of the more typical means for accomplishing tooth movement is by employment of band and arch wire assemblies, wherein the teeth to be moved are encircled with bands of thin metal that is cemented to the teeth and dental appliances, which may take the form of arch wire brackets or any of numerous other connecting devices may be affixed to or formed integrally with the band structure. An arch wire, which may be of round or rectangular configuration when viewed in cross section, may be received by the various brackets protruding from the bands encircling the teeth to be moved. Springs, elastic bands, and numerous other devices may be employed to apply forces to the various teeth to be moved within the rather porous craniofacial skeletal structure of the patient. As forces are applied to the teeth, during orthodontic therapy, the mechanical pressure applied between the teeth and the bone structure causes tooth drift, which, in simple terms, results from addition of bone structure on one side of the tooth and resorption on the opposite side. Orthodontic appliances are employed to produce a force that will elicit optimum tissue response within the periodontal ligament and bone structure of the patient thereby resulting in permanent repositioning of the patients teeth, as desired. The orthodontic appliance is a force system that stores and delivers forces against the teeth, muscles, or bone and creates a reaction within the periodontal ligament and alveolar bone that permits movements of the teeth relative to the bone structure, which movement is of permanent nature because it is accomplished by induced tooth drift that results in controlled reformation of the bone structure.

Orthodontic treatment often involves removal of at least some of the patient's teeth in order to gain the space that is necessary for optimum positioning of the remaining teeth, but tooth removal is accomplished only when absolutely necessary to provide for optimum spacing. There are cases however, when the normal spacing of a patient's teeth is proper and tooth removal is inappropriate, but there is insufficient space to accommodate the combined thicknesses of the thin bands that normally encircle the teeth during treatment. Under this condition, removal of some of the patient's teeth may result simply to accommodate the bands that are necessary during treatment. Because of the undesirability of removing teeth simply to provide the space necessary for the orthodontic bands, it is considered desirable to provide means other than bands for support of the brackets and other orthodontic appliances that are utilized to impart forces to the teeth for movement of the same within the bone structure of the patient. In the past, metal brackets and other orthodontic appliances have been bonded directly to the enamel surface of the patient's teeth in position for optimum connection with arch wires and other orthodontic devices. Direct attachment of metal brackets to the tooth structure has not been satisfactory because of the difficulty of providing a bond between a metal surface and the enamel surface of the tooth. Thus far, no bonding agent has been found that will provide a desirable and controllably releasable bond between metal brackets and the enamel of the teeth.

Direct bonding of metal brackets to the tooth structure is also undesirable from the standpoint of removal of the brackets or appliances after completion of orthodontic treatment. If the bond between the metal and enamel is sufficient to retain the same in assembly during treatment, the bonding material will typically refuse yield readily after treatment and it is possible to damage the enamel as to the metal is separated from the enamel. Removal of the metal structure from the enamel by grinding or other mechanical operations is not conveniently possible because of the heat that is generated and because of the susceptability of the teeth to damage by metal working tools.

Another disadvantage of the conventional band type method of accomplishing orthodontic treatment is the problem of tooth decalcification that frequently occurs during treatment. The cement that is typically employed to attach the bands to the individual teeth is typically susceptible to being disolved by the action of the saliva, thereby causing spaces to develop beneath the bands and these spaces are usually not detectible. The spaces beneath the bands can accumulate food product, and, because of the action of the saliva thereon, the food product will develop an acid that causes demineralization of the tooth structure. In some cases, caries will develop because of the action of the acid in the spaces under the bands, but the most typical result is demineralization, which develops tooth discoloration that logically detracts from the aesthetic appearance of the teeth.

Conventional orthodontic bands also have rather sharp marginal edges and protrusions that may constantly irritate the gingiva, causing pain to the patient and detracting from the ability of the patient to keep his teeth hygenically clean during the period of orthodontic treatment. Infection of the gingiva is a constant problem when orthodontic treatment is conducted with metal bands about the teeth.

Brackets and other orthodontic appliances composed of plastic material have been successfully bonded to the enamel surface of teeth to provide for orthodontic treatment primarily because the plastic material may be removed quite effectively following orthodontic treatment without any risk of damage to the tooth structure. Plastic brackets and appliances however are considered undesirable from the standpoint of application of forces to the teeth to be moved. For example, most plastic materials are yieldable under mechanical pressure. Although the mechanical pressure that is applied to the teeth during orthodontic treatment is quite low, i.e., in the order of 5 to 15 ounces, the mechanical pressure that is applied in point to point contact between the arch wire and the bracket is quite high. When brackets are composed of plastic material, the mechanical force reacting against the plastic tends to cause the plastic to yield or cold flow, thus causing the application of forces to the tooth structure to diminish quite rapidly after having been properly set by an orthodontist during installation or adjustment of the same. It is desirable therefore to provide non-yieldable contact, such as metal-to-metal contact between the arch wire and bracket structures, but to provide means for effectively attaching the metal bracket structures to the tooth structure in such a manner that the bracket can be readily removed from the tooth structure when desired.

The caulk division of Dentsply International, Inc. of Milford, Delaware, has proposed a method of attaching a metal orthodontic bracket to the enamel surface of teeth wherein the tooth surface is prepared by acid etching and a coating of a dental sealer material is applied to the etched surface and hardened. After this has been done, a dental filler material may be applied to the cured sealer material and an orthodontic bracket may be brought into assembly with the uncured filler material in such manner that the filler material protrudes through apertures formed in the bracket structure. The dental filler material then may be cured in place, thereby causing the bracket or other orthodontic appliance to be permanently affixed to the tooth structure. Removal of the metal bracket from the enameled surface of the tooth is accomplished simply by cutting or machining away the dental filler material protruding through the apertures of the bracket thereby destroying the mechanical interlocking relationship between the metal and the dental filler material, whereupon the metal bracket or other orthodontic appliance may be simply removed. After removal of the bracket, the remaining dental filler material and coating may be removed by conventional machining operations. This method of attachment is not entirely satisfactory because the dental filler material, protruding through the apertures of the bracket, tends to interfere with connection wires that are typically employed to establish firm connection between the bracket and arch wire assembly.

It is therefore a primary object of the present invention to provide a novel orthodontic appliance assembly wherein orthodontic appliances such as brackets and other mechanical device may be fixed to the exterior enamel surface of the patient's teeth without necessitating employment of conventional orthodontic bands.

It is another object of the present invention to provide a novel orthodontic appliance assembly that may be simply applied and removed from the tooth structure without any damage to the tooth structure when such removal is desired.

It is an even further object of the present invention to provide a novel orthodontic appliance assembly employing a metal orthodontic bracket or other appliance that will establish nondeforming mechanical interconnection between force applying parts of the orthodontic assembly.

It is another object of the present invention ro provide a novel orthodontic appliance assembly that may be simply and effectively removed from the tooth structure of the patent when removal is desired.

Smong the several objects of the present invention is noted the contemplation of a novel orthodontic appliance assembly that facilitates effective movement of teeth under circumstances when there is minimal spacing between the teeth and it is not appropriate to remove teeth to provide additional spacing.

It is also an important object of the present invention to provide a novel orthodontic appliance assembly that may be attached to the tooth structure of the patient in a movable manner and may be shifted as desired to provide proper alignment with respect to other orthodontic appliance assemblies before being controllably and immovably bonded in place.

It is an even further object of the present invention to provide a novel method for attaching orthodontic brackets and other orthodontic appliances to the enamel surfaces of the teeth of patients.

Other and further objects, advantages and features of the present invention will become apparent to one skilled in the art upon consideration of this disclosure. The form of the invention, which will now be described in detail, illustrates the general principles of the invention, but it is to be understood that this detailed description is not to be taken as limiting tthe scope of the present invention.

SUMMARY OF THE INVENTION

A preferred embodiment of the present invention may conviently take the form of a thin veneer body of non-metallic material such as any one of a number of suitable plastic materials, which veneer body is shaped to conform to a portion of the exterior surface of the tooth to which it is to be attached. An orthodontic appliance, having a base portion and an active portion that are interconnected by means of a support portion, may be structurally interconnected with the thin veneer body prior to attachment of the same to the tooth structure of the patient. The thin veneer body, with the orthodontic appliance attached, is pre-formed and the material supporting the orthodontic bracket or appliance is fully cured before it is attached to the patient's tooth structure.

The base portion of the orthodontic appliance may be provided with a plurality of apertures through which the material of the veneer may extend thereby establishing a positive interlocking relationship between the orthodontic appliance and the veneer body. Additionally, the base portion of the bracket or other orthodontic appliance may be provided with rounded edges that cooperate with the material from which the veneer body is composed to prevent development of excessive areas of strain within the thin veneer body. The base portion may be imbedded within the fully cured veneer body and the support portion may protrude from the veneer body and may provide support for the active portion of the appliance. The active portion may conveniently take the form of an orthodontic bracket or any one of numerous other orthodontic fixtures within the spirit and scope of the present invention.

Attachment of the thin veneer body, with its orthodontic appliance fixed thereto, to the tooth structure of the patient may be accomplished simply by placement of the veneer body into assembly with the tooth structure in order to assure proper fitting relationship therebetween. After it has been ascertained that the veneer body will fit the exterior enamel surface of the tooth, that portion of the tooth structure to which the veneer body is to be attached may be etched with a weak acid solution such as citric acid. After this has been accomplished, the beneer body may be brought into engagement with the tooth in the presence of a bonding agent to complete the attachment procedure. As an alternative, the etched surface of the tooth and the internal surface of the thin veneer body may be coated with a dental sealer material and these coatings may be appropriate cured in place. After curing of the coating, a quantity of dental filler material may be applied either to the coated interior surface of the veneer body or to the coated surface of the tooth and the veneer body may be brought into assembly with the tooth. Sufficient mechanical force may be applied to squeeze out excess dental filler material, thus causing all of the voids between the coated surfaces of the tooth and the veneer body to be filled with the dental filler material. The dental filler material may be controllably cured in place to bond the veneer body to the tooth structure at this point, or bonding of the dental filler material may be accomplished after all or most of the orthodontic appliances have been assembled to the respective teeth of the patient and have been appropriately aligned with other orthodontic appliances. In this case, all of the veneer bodies applied to the various teeth may be controllably cured simultaneously. After the veneer bodies and the orthodontic appliances supported thereby have been bonded to the tooth structure, a coating of dental sealer material may be applied to the exposed surfaces of the thin veneer body to establish a positive seal at the marginal edges of the veneer body to prevent marginal leakage that might otherwise provide an environment that is not conductive to oral hygiene.

BRIEF DESCRIPTION OF THE DRAWINGS

So that the manner in which the above recited features, advantages and objects of the present invention, as well as others, which will become apparent, are attained and can be understood in detail, more particularly description of the invention, briefly summarized above, may be had by reference to the embodiments thereof which are illustrated in the appended drawings, which drawings form a part of this specification.

It is to be noted however that the appended drawings illustrate only one of numerous orthodontic appliance assemblies that are made possible by employment of the method and materials set forth herein and is therefore not to be considered limiting of its scope, for the invention may admit to other equally effective embodiments without departing from the spirit and scope of this invention.

IN THE DRAWINGS

DESCRIPTION OF PREFERRED EMBODIMENT

Figures 1, 4:
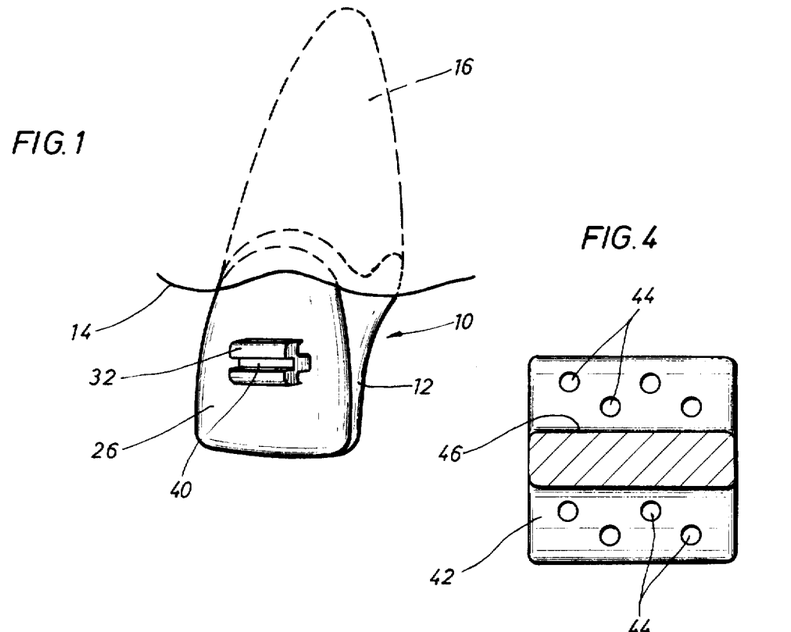
FIG. 1 is a pictorial representation of a tooth that is to be moved by orthodontic treatment and to which tooth is affixed an orthodontic appliance assembly constructed in accordance with the present invention.
FIG. 4 is a partial sectional view of an orthodontic bracket or other orthodontic appliance illustrating apertures found in the base portion of the bracket to establish physical connection with the material from which the thin veneer body is composed.

Now referring to the drawings and first to FIG. 1, the present invention may take the form of an orthodontic appliance assembly, together with a method for temporarily attaching the orthodontic appliance assembly to the tooth structure of a patient whose teeth are to be shifted in accordance with orthodontic principles. A tooth structure, illustrated generally at 10 in FIG. 1, which tooth is shown to be an anterior incisor, is shown with the crown portion 12 of the tooth extending from the gingiva or gum while the root portion 16 of the tooth structure, shown in broken line, is of course, embedded and supported by the bone structure of the patient.

Figure 2:
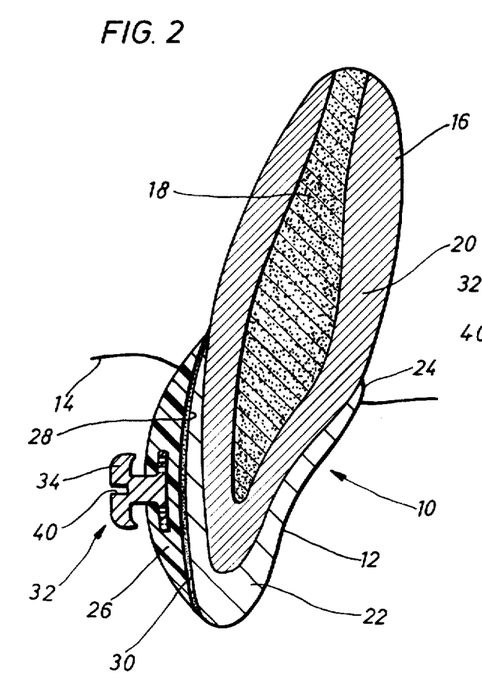
FIG. 2 is a sectional view of a tooth structure such as that set forth in FIG. 1 also illustrating a sectional view of the orthodontic appliance, assembly attached to the tooth structure, and which assembly in this case takes the form of an orthodontic bracket for assembly with an orthodontic arch wire.

As shown in section in FIG. 2, the tooth structure incorporates an inner pulp portion 18 surrounded by dentin with the dentin being surrounded in the crown portion of the tooth by a layer of enamel 22. The enamel meets with the dentin at the juncture between the crown and root portion of the tooth defining a rather abrupt shoulder 24.

In order to shift the tooth 10 within the rather porous bone structure of the patient, it is desirable to apply light mechanical pressure gradually and over a long period of time in order that a pressure responsive condition of bond adsorption and deposition may occur that causes controlled permanent drift of the tooth to occur within the bone structure. It is desirable to apply mechanical pressure in such manner that the periodontal ligament surrounding the tooth structure and interposed between the tooth structure and bond structure in the alveolar socket will not be overstressed or overcompressed during translation or bodily movement of the tooth. Mechanical forces may also be applied to cause tipping of the teeth, wherein the crown and root of the tooth are moved in opposite directions around a center of rotation within the root or torque may be applied to a tooth to cause rotation of the tooth around its long axis. Other tooth movement such as intrusion and extrusion wherein movement of the tooth is either inwardly or outwardly relative to the alveolar socket may be accomplished by similar application of mechanical force over long periods of treatment. Moreover, if torque is applied in the orthodontic sense, the purpose is to obtain movement of the root portion of the tooth without consequent movement of the crown. This is caused by a tipping movement with the fulcrum of movement in the bracket.

As illustrated pictorially in FIG. 1 and in section in FIG. 2, a rather thin body of fully cured material having substantial structural integrity may be adhered directly to the labial surface 28 of the crown portion of the tooth and may, if desired, cover substantially the entire labial surface of the tooth essentially as shown in FIGS. 1 and 2. The pre-formed thin veneer body or lamination 26 that is to be bonded to the tooth structure during orthodontic treatment in accordance with the methods set forth herein, may conveniently take any suitable form that is acceptable for the establishment of a good mechanical bond with the tooth structure. It has been found through initial tests that a plastic material such as fully polymerized, pre-formed methyl methacrylate is a suitable material from which the thin veneer body may be composed. Methyl methacrylate is utilized presently in the manufacture of denture teeth and therefore corresponds very closely to the appearance and functional capabilities of natural teeth. Other materials, such as polycarbonate plastics and acrylate plastics, for example, may also be successfully employed to define veneer bodies for attachment to the patients teeth in accordance with this invention. It is envisioned that the thin veneer body structure may be premanufactured according to various shapes, forms, colors, and contour in order to conform to the particular characteristics of the teeth to which the thin veneer body is to be applied. Moreover, the thin veneer body may be flexible in order to conform to the configuration of the teeth to which it is to be applied and may also be formed to define thin knifelike edges in order that a smooth configuous surface may be established at the joint between the enamel surface of the tooth and the veneer body. The plastic veneer may be of tooth color, giving a much better and esthetically pleasing appearance during orthodontic treatment as compared to metal handed teeth or it may be clear, so the condition of the enamel may be monitored during treatment to prevent demineralization of the tooth structure. The material from which the veneer body is composed may also be easily machinable in order that minor differences in contour between the facing and the external configuration of the tooth may be accommodated by simple machining that can be accomplished while the patient is sitting for installation of the orthodontic appliance assembly.

The thin veneer body, if desired, may be composed of very thin flexible material that may be readily molded by application of mechanical pressure, thereby causing the flexible veneer body to conform to the tooth surface to which it is to be attached. For example, it may be desirable to provide a flexible and moldable plastic veneer body that may be molded to conform to selected surfaces of the tooth. If desired, the thin veneer body may be of such flexibility and curvature that it may be utilized all or part of the labial surface of the tooth and may additionally cover one or more of the proximal edges.

As shown in FIG. 2, the thin veneer body 26 may be bonded to the labial surface of the tooth, by a bonding material that may be any one of a number of commercially available bonding materials without departing from the spirit or scope of the present invention. One suitable bonding material for example, may be of the type that is produced by the reaction product of bisphenol A and glycidyl methacrylate and which is activated by benzoin methyl ether catalyst and polymerized responsive to application of ultra-violet light and which is manufactured by the Caulk Division of Dentsply International, Inc. and sold under the registered trademark "Nuva-Tach".

It will be desirable to establish a mechanical connection between the thin veneer body 26 and other orthodontic devices such as arch wires, for example, and to provide a mechanical structure that will not yield as pressure is applied over long periods of time. In accordance with the present invention, an orthodontic appliance may be partially imbedded in the thin veneer body and may have an active portion thereof protruding from the veneer body and positioned for mating relationship with other orthodontic devices. As shown in FIG. 2 and also in FIG. 3, for example, an orthodontic bracket is illustrated generally at 32 having an active portion 34 that is in the form of an elongated generally rectangular head having opposed wire retaining flanges 36 and 38 formed integrally therewith. The head portion or active portion of the bracket 32 is shown to be adapted to receive an arch wire that is positioned within an elongated groove 40 defined in the head 34. The groove 40 is shown to be a rectangular cross sectional configuration to receive an arch wire of mating rectangular cross sectional configuration, but this particular structure is not intended to limit the present invention in any way, it being obvious that arch wire grooves of other than rectangular configuration may be provided without departing from the spirit and scope of the present invention. It is also within the spirit and scope of the present invention to employ mechanical devices other than orthodontic brackets that are supported by the thin veneer body 26 in similar manner.

Figure 3:
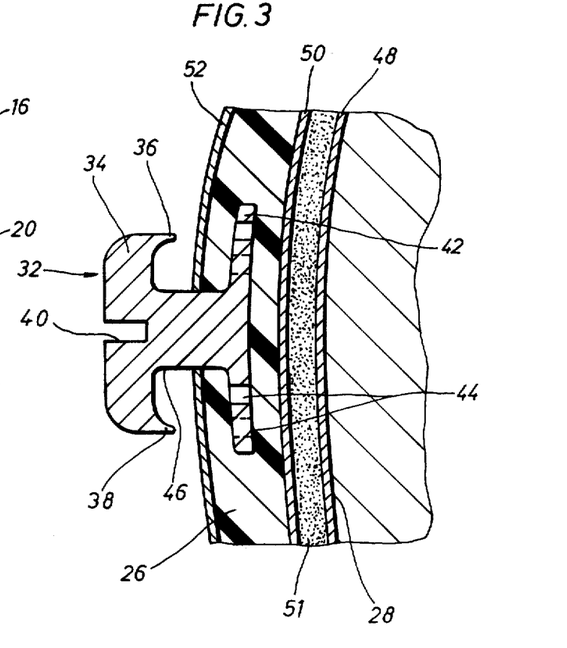
FIG. 3 is a fragmentary enlarged sectional view of a portion of a tooth structure such as shown in FIG. 1, illustrating the component parts of an orthodontic appliance assembly constructed in accordance with this invention and depicting attachment of the orthodontic appliance assembly to the tooth structure utilizing dental sealer and filler materials as bonding agents.

The orthodontic appliance supported by the thin veneer body 26 may incorporate a base portion 42 that is shown in FIG. 3 as being slightly curved to conform to the configuration of the veneer body and the exterior surface of the tooth and which is shown in FIG. 4 as being generally rectangular in configuration. The base portion 42 may have rounded corners and edges that cooperate with the material from which the veneer body is composed to prevent overstressing of any particular part of the veneer, thus allowing the base portion of the appliance to be positively and unyieldingly supported by the veneer body during an entire orthodontic procedure. Further, as illustrated in FIGS. 3 and 4, the base portion 42 of the orthodontic appliance or bracket 32 may have a plurality of apertures 44 defined therein which apertures provide for development of an interlocking relationship with the cured material from which the thin veneer body 26 is composed. As the veneer body is molded during manufacture thereof, the material from which it is composed during the uncured state will flow through the apertures 44 and will cooperate with the generally rectangular configuration of the base portion of the bracket to define a positive mechanically interlocked integral relationship between the base portion of the bracket and the thin veneer body. After the composition of the veneer body has fully cured, the veneer body and the base portion of the orthodontic appliance will be substantially integral.

A connecting element such as an elongated generally rectangular connector 46 may be formed integrally with the head portion and base portion of the orthodontic appliance or may be connected between the head and base portions of the orthodontic appliance in any suitable manner to provide a supported relationship between the head and base portions.

Although it may be desirable simply to establish a mechanical connection between the thin veneer body 26 and the labial surface 28 of the tooth with a bonding agent as illustrated in FIG. 2, it may also be desirable to employ dental sealer and filler materials as bonding agents in the manner illustrated in FIG. 3 in order to take advantage of the sealing and filling qualities thereof as well as taking advantage of the bonding function provided by the same. It will also be desirable to prepare the labial surface of the tooth for bonding with some suitable process that provides an appropriate enamel surface for retention of the bonding material. For example, a small portion or the entire labial surface of the enamel of the tooth may be prepared in such a way as to remove undesirable mineral deposits that might interfere with the bonding process. This may be accomplished by very light sanding. Desired portions of the exposed enamel then may be prepared for bonding by application of a suitable acid material such as a weak solution of citric acid for a short period of time. This is known in the art as acid etching, a process that creates spaces or "micro pores" within the surface layer of enamel which will allow the dental sealant material to penetrate into the surface of the enamel itself and establish an efficient mechanical interlocking bond with the enamel. As the tooth is etched, projections, which may be referred to as "rods" or "tags" are developed which increase the physical bonding of the sealant to the tooth structure. The employment of acidic conditioning agents has an effect on the tooth enamel that removes at least a portion of the mineral salts from the enamel surface to a very shallow depth, i.e., in the order of 25 microns, thereby creating spaces or micro pores in the enamel where the mineral salts have been dissolved. Etching of the tooth enamel, although initially creating a dull appearance on the enamel surface, does not constitute permanent alternation of the enamel surface of the tooth. In fact, areas of enamel surface that have been etched, if not covered by a coating of dental sealant material, will return to the normal translucency thereof within a few days' time. It is theorized that acid etched enamel is remineralized by the deposition of calcium phosphate salts from the saliva. Other than the creation of a superficial etch, there appears to be no detrimental effect on the tissue of the tooth. After acid etching of desirable portions of the enamel of the tooth structure, the acid etched enamel is maintained clear of any material such as water, oil, saliva, etc., that might interfere with the bonding process, and a dental sealant material may be applied thereto and may be allowed to subsequently become catalized in place in order to seal the micro pores that have been established by the etching process and to establish a physical surface to which the thin veneer body may be effectively bonded. Although the dental sealant material may take any suitable form within the spirit and scope of the present invention, it may be desirable to employ a dental sealant material such as that sold under the trademark "Nuva-Seal" by the Caulk Division of Dentsply International, Inc., which is referred to hereinafter merely as a dental sealer or dental sealing material. The dental sealing material may be of the type that is produced by the reaction product of bisphenol A and glycidyl methacrylate such as a product manufactured and sold under the trademark Nuva-Seal by the Caulk Division of Dentsply International, Inc., of Milford, Delaware. The sealant product, referred to as Nuva-Seal, is activated by benjoin methyl ether catalyst prior to the application thereof to a tooth structure and is polymerized after application to the surface by exposure to ultraviolet light.

After etching that portion of the enamel that is to receive the thin veneer body, a coating of dental sealant material 48 may be applied directly to the prepared enamel surface and may be cured in place by exposing the applied coating to ultra-violet light. After this has been done, the interior surface of the thin veneer body may also be provided with a coating 50 of dental sealant material and this coating may also be cured in place by exposure to ultra-violet light. The thin veneer body, having been previously coated on the inside surface thereof, is now ready for application to the prepared surface of the tooth, but it is desirable that there be no voids between the inside surface of the veneer body and the prepared and coated exterior surface of the tooth structure. For the purpose of filling all of the voids, a quantity of dental filler material 51, which may also be a reaction product of bisphenol A and glycidyl methacrylate and which is also activated by benjoin methyl ether catalyst and selectively polymerized by exposure to ultra-violet light, may be applied either to the prepared outer surface of the tooth structure or to the prepared inner surface of the thin veneer body. The dental filler material will typically have a fairly thick, paste-like consistency as compared to the rather "wet" thin consistency of the dental sealer material. The dental filler material identified above is sold by the Caulk Division of Dentsply International, Inc., under the trademark "Nuva-Fil". It is not intended to limit the present invention to use of these particular dental sealer and filler materials, however, it being obvious that other sealer and filler materials as well as other bonding agents may be effectively employed within the spirit and scope of this invention. Cyanoacrylate bonding agents and self curing acrylic resins are exemplary of the many commercially available bonding agents that may be successfully employed to carry out this invention.

The veneer body 26 is then brought into assembly with the tooth structure with the uncured dental sealant material disposed therebetween, the dental filler material being of a relatively thick paste-like consistency. Sufficient mechanical pressure is applied manually to squeeze out most of the dental filler material between the prepared surfaces of the tooth and veneer body and the dental filler material that is so displaced may be removed from about the marginal edges of the veneer body with a simple smoothing tool. In order to provide as much control as possible, to insure the establishment of properly interrelated relationships between the various orthodontic appliance assemblies of other teeth of the patient, it may be desirable to refrain from curing the dental sealant material until all of the orthodontic appliances have been placed in assembly with the various teeth.

After proper alignment of the various orthodontic appliance assemblies has been insured, the dental sealer material may be polymerized simply by exposing the same to ultra-violet light and this polymerization process positively bonds the thin veneer body 26 to the coated and prepared surface of the tooth.

In view of the fact that the orthodontic appliance assembly may remain in supported relationship with the tooth structure for long periods of time, it is desirable to prevent any marginal leakage between the veneer body and the tooth structure. Accomplishment of the same may conveniently take the form of a coating 52 of dental sealant material that may be applied to the outer exposed surface of the thin veneer body, which coating may also cover the joint defined between the marginal edges of the veneer body and the enamel surface of the tooth. The dental sealant material defining the coating 52 may be of the same character and type as employed to define the coatings 48 and 50, but may take other suitable forms as is desired without departing from the spirit and scope of the present invention.

By employing dental sealant and filler materials such as those sold by the Caulk Division of Dentsply International, Inc., under the trademarks Nuva-Fill and Nuva-Seal, the dental sealer and filler material will not become polymerized until polymerization is controllably induced. The dental filler and sealer therefore may be worked for whatever period of time is necessary to properly shape the unpolymerized dental filler and sealer materials about the thin veneer body portion of the orthodontic appliance assembly and polymerization will occur in a few seconds time after application of ultra-violet light to the shaped material.

It is not intended however to limit the present invention solely to the use of ultra-violet light activated dental sealer and filler materials, it being obvious that other dental sealer and filler materials may be employed within the spirit and scope of the present invention.

Figures 5, 6, 7:
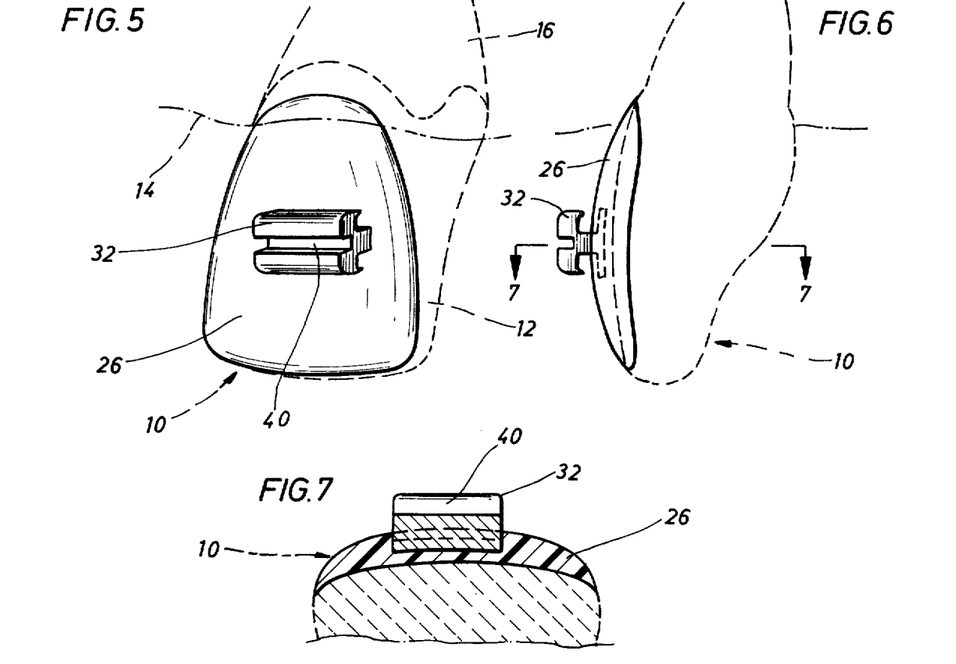
FIG. 5 is a pictorial representation of an orthodontic appliance assembly constructed in accordance with the present invention and shown in full line while showing a portion of a tooth structure to which the same is to be attached in broken line.
FIG. 6 is a side view of the orthodontic appliance assembly of FIG. 5, also illustrating the tooth structure to broken line.
FIG. 7 is a sectional view taken along line 7—7 of FIG. 6.

As illustrated in FIGS. 5, 6, and 7, orthodontic appliance assemblies for temporary attachment to the labial surfaces of teeth may be designed to cover the entire labial surface, thereby providing an optimum structural interrelation between the tooth structure and the structure of the veneer body to transmit forces applied through the orthodontic appliance to the veneer body and consequently to the tooth structure. Although the thin veneer body is shown in the various figures as being applied to the labial surface of the tooth structure, it is to be borne in mind that suitably formed veneer bodies carrying orthodontic appliances may be effectively bonded to any other desirable portions of the tooth structure within the spirit and scope of the present invention.

Figure 8:
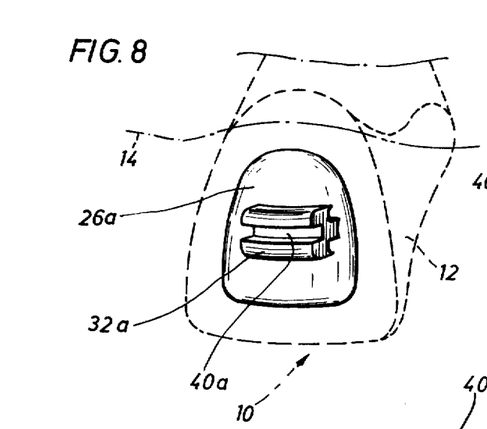
FIG. 8 is a pictorial representation in broken line of a portion of the tooth structure of a patient, having an orthodontic appliance assembly constructed in accordance with the present invention affixed thereto, the thin veneer body of which is of significantly smaller dimension than the labial surface of the tooth.
Figure 9:
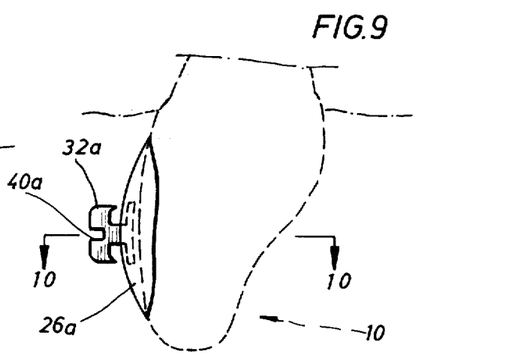
FIG. 9 is a side view of the tooth and orthodontic appliance assembly shown in FIG. 8, with the tooth structure and the base portion of an orthodontic bracket being shown in broken line and with the remaining portions of the orthodontic appliance assembly being shown in full line.
Figure 10:
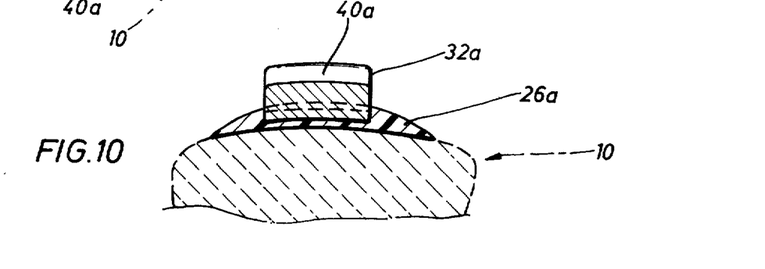
FIG. 10 is a sectional view taken along line 10—10 of FIG. 9.

As illustrated in FIGS. 8, 9 and 10, the orthodontic appliance assembly may conveniently take a smaller form than the dimension of the labial surface area of the tooth structure. The veneer body 26a in this case will be of sufficient dimension to provide proper mechanically locked interrelation between the veneer body and the tooth structure and to withstand the forces applied thereto during orthodontic treatment. The veneer body 26a may be formed to conform to that portion of the tooth structure to which it is to be applied and may include knife-like marginal edges that coincide smoothly with the enamel surface of the tooth structure. The orthodontic appliance assembly that covers only part of the labial surface of the tooth, may be connected to the enamel surface of the tooth simply by bonding with any suitable bonding material or, in the alternative, it may be secured to the tooth structure utilizing dental sealer and filler materials in the manner identified above. The partial laminations defined by the thin veneer body may have embedded therein and protruding therefrom any number of different types of orthodontic appliances including orthodontic brackets as shown.

After orthodontic treatment has been completed or when it is desired to remove the orthodontic appliances from at least some of the teeth, this can be accomplished simply and efficiently simply by scraping the non-metalic or plastic material from the surface of the tooth with a sharp instrument or by machining away the plastic material about the base portion of the orthodontic appliance thereby allowing the metallic appliance to be easily extracted from its seated position relative to the plastic material of the thin veneer body. After the metal appliance structure has been removed, the remaining portion of the plastic material may be simply machined from the surface of the tooth and the tooth will be restored to its original condition. Removal of orthodontic appliances of this nature, from individual teeth takes only a few seconds' time.

In view of the foregoing it is apparent that I have provided a unique orthodontic appliance assembly for attachment to the tooth structure of a patient that is involved in orthodontic treatment, which appliance may be very easily and simply applied to the tooth structure in readily controlled manner, thereby enabling a number of orthodontic appliance assemblies to be precisely oriented, taking as much time as desired for such orienting, before a firm bond is established between the orthodontic appliance assembly and the tooth structure. The orthodontic appliance assembly I have provided, utilizes metallic connector elements for connection with other orthodontic devices, and therefore will not yield or cold flow as in the case of plastic brackets and will not become worn during ordinary use to the point that replacement is necessary before the orthodontic procedure is completed.

I have also provided a unique method for attachment of veneer supported orthodontic appliances to the tooth structure of patients, utilizing dental sealer and filler materials in a controlled manner to accomplish optimum support as well as in appearance. The orthodontic appliance assemblies, once firmly attached to the tooth structure, will serve unyieldingly throughout a protracted orthodontic procedure and, when removal is desired, may be removed quite simply and efficiently in a few seconds' time by simple mechanical operations.

It is therefore apparent that the present invention is one well adapted to attain all the objects and advantages hereinabove set forth, together with other advantages which will become obvious and inherent from a description of the apparatus and method utilized in accordance with the teachings of the present invention. It will be understood that certain combinations and subcombinations are of utility and may be employed without reference to other features and subcombinations. This is contemplated by and is within the scope of the present invention.

As many possible embodiments may be made of this invention without departing from the spirit or scope thereof, it is to be understood that all matters hereinabove set forth are shown in the accompanying drawings are to be interpreted as illustrative and not in a limiting sense.

What is claimed is:

1. An orthodontic appliance assembly for attachment to the tooth structure of a patient, said orthodontic appliance assembly comprising:
    a fully cured pre-formed thin veneer body of plastic material, said veneer body defining a concave interior surface that is shaped to conform to a portion of the exterior surface area of at least one of the patients teeth and defining an exterior surface that conforms to the natural configuration of the teeth of the patient; and
    an orthodontic appliance, said appliance having a base portion and an active portion, said base portion being formed to define plastic interlocking means, said base portion being molded within said thin veneer body and said plastic material being interconnected with said base portion and firmly supporting said base portion, said active portion of said appliance protruding from said veneer body and having an orthodontic connector portion formed thereon, said connector portion being of generally T-shaped crosssection defining an arch wire slot and defining opposed wire retaining flanges for receiving ligature wires, said connector portion of said orthodontic appliance being spaced from the exterior surface of said thin veneer body.

2. An orthodontic appliance assembly as recited in claim 1, wherein:
    said thin veneer body has knife-like edges formed about at least a portion thereof, said knifelike edges being disposed for contact with the exterior surface of the patients tooth and cooperating with said exterior surface of the patients tooth to define a smooth marginal joint between said thin veneer body and said exterior surface of said tooth.

3. An orthodontic appliance assembly as recited in claim 1, wherein:
    said thin veneer body is flexible and conforms readily to the contour of the patients tooth for which it is formed; and
    said thin veneer body has knife-like edges formed about at least a portion of the peripheral portion thereof, said knife-like edges being disposed for contact with the exterior surface of the patients tooth and cooperating with said exterior surface of the patients tooth to define a smooth marginal joint between said thin veneer body and said exterior surface of said tooth.

4. An orthodontic appliance assembly as recited in claim 1, wherein:
    said thin veneer body is of sufficient size, relative to the size of the tooth of the patient for which the veneer body is intended, to cover substantially all of the labial surface area of the tooth of said patient.

5. An orthodontic appliance assembly as recited in claim 1, wherein:
    said thin veneer body is of smaller size than the size of the labial surface of the tooth of said patient.

6. An orthodontic appliance assembly as recited in claim 1, wherein:
    said veneer body is preformed of fully cured material before application thereof to the exterior surface of the tooth of said patient;
    said thin veneer body is flexible and conforms readily to the contour of the patients tooth to which it is to be applied; and
    said thin veneer body has knife-like edge formed about at least a portion of the peripheral portion thereof said knife-like edges being disposed for contact with the exterior surface of the patients tooth and cooperating with said exterior surface of the patients tooth to define a smooth marginal joint between said thin veneer body and said exterior surface of said tooth.

7. An orthodontic appliance assembly as recited in claim 1, wherein:
    said base portion of said orthodontic appliance has rounded edges formed thereon that function in conjunction with the material from which said thin veneer body is formed to prevent the formation of excessively stressed areas in said material as forces are applied to said orthodontic appliance.

8. An orthodontic appliance assembly as recited in claim 1, wherein:
    said base portion of said orthodontic appliance is of generally rectangular configuration;
    said active portion of said orthodontic appliance is of a configuration that cooperates with other orthodontic appliance structure utilized for imparting moving to the patients teeth relative to the bond structure of the patient; and
    connecting means of smaller dimension than the dimension of said base portion and said active portion between said base portion and said active portion of said orthodontic appliance, said connection means being partially molded within said veneer body.

9. In combination with the tooth structure of an orthodontic patient:
    a thin veneer body of fully cured stain resistant plastic material, said veneer body defining a concave interior surface that is shaped to conform to a portion of the exterior surface area of at least one of the teeth of said patient and defining an exterior surface that conforms to the natural configuration of the labial surface of said one of the teeth of said patient;
    an orthodontic appliance having a base portion and an active portion, said base portion being formed to define plastic interlocking means, said base portion said active portion protruding from said veneer body, said orthodontic appliance having a connecting portion of smaller dimension than the dimension of said active portion and said base portion and being at least partially molded within said thin veneer body and having an orthodontic connector portion formed thereon, said connector portion being of generally T-shaped cross-section defining an arch wire slot and defining opposed wire retaining flanges for receiving ligature wires, said connector portion of said orthodontic appliance being spaced from the exterior surface of said thin veneer body; and bonding material being disposed between said veneer body and said exterior surface area of said tooth filling any voids between the veneer body and the tooth and bonding said thin veneer body to the exterior surface of said tooth.

10. The combination of claim 9, wherein said bonding material comprises dental sealer material.

11. The combination of claim 9, wherein said bonding material comprises:

dental sealer material coating adjacent surfaces of said tooth and said thin veneer body; and dental filler material filling the voids between said coated adjacent surfaces.

12. The combination of claim 11, wherein:

said dental sealer material is composed of material being the reaction product of bisphenol A and glycidyl methacrylate activated by benzoin methyl ether catylist and polymerized after exposure to ultra-violet light; and said dental filler material is composed of material that is substantially chemically identical to the composition of said dental sealer material and is of thicker consistency in the unpolymerized state as compared to said dental sealer material.

13. The combination of claim 9, wherein:

said thin veneer body is bonded directly to the enamel surface a tooth of said patient.

* * * * *